(12) United States Patent
Lead et al.

(10) Patent No.: US 9,835,628 B2
(45) Date of Patent: Dec. 5, 2017

(54) CORE-SHELL NANOPARTICLES COMPRISING SAME ELEMENT OF DIFFERENT ISOTOPES

(71) Applicant: University of South Carolina, Columbia, SC (US)

(72) Inventors: Jamie Lead, Chapin, SC (US); Ruth Merrifield, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/695,083

(22) Filed: Apr. 24, 2015

(65) Prior Publication Data
US 2015/0309043 A1 Oct. 29, 2015

Related U.S. Application Data

(60) Provisional application No. 61/983,807, filed on Apr. 24, 2014.

(51) Int. Cl.
| | |
|---|---|
| *B22F 1/02* | (2006.01) |
| *G01N 33/58* | (2006.01) |
| *B01J 23/52* | (2006.01) |
| *B01J 35/00* | (2006.01) |
| *C23C 30/00* | (2006.01) |
| *B22F 1/00* | (2006.01) |
| *C23C 28/00* | (2006.01) |
| *C23C 28/02* | (2006.01) |
| *B01J 37/02* | (2006.01) |

(Continued)

(52) U.S. Cl.
CPC ............ *G01N 33/587* (2013.01); *B01J 23/06* (2013.01); *B01J 23/50* (2013.01); *B01J 23/52* (2013.01); *B01J 35/002* (2013.01); *B01J 35/008* (2013.01); *B01J 35/0013* (2013.01); *B01J 35/0086* (2013.01); *B01J 37/0244* (2013.01); *B22F 1/0018* (2013.01); *B22F 1/0088* (2013.01); *B22F 1/025* (2013.01); *C23C 28/023* (2013.01); *C23C 28/42* (2013.01); *C23C 30/00* (2013.01); *B01J 23/66* (2013.01); *B01J 33/00* (2013.01); *B01J 35/0033* (2013.01); *B01J 37/16* (2013.01); *B82Y 15/00* (2013.01); *B82Y 30/00* (2013.01); *Y10S 977/773* (2013.01)

(58) Field of Classification Search
CPC .... C08K 2003/0805; C08K 2003/0831; B82Y 30/00; C23C 28/023; C23C 28/42; C23C 30/00; B22F 1/0018; B22F 1/0088; B22F 1/025
USPC .......................................... 428/547, 548, 570
See application file for complete search history.

(56) References Cited

U.S. PATENT DOCUMENTS

2009/0246143 A1* 10/2009 Bonitatibus, Jr. .. A61K 49/1848
424/9.32

OTHER PUBLICATIONS

Lu et al, Stable silver isotope fractionation in the natural transformation process of silver nanoparticles, Nature Nanotechnology, vol. 11, 2016, 682-686.*

(Continued)

*Primary Examiner* — Holly Le
(74) *Attorney, Agent, or Firm* — Dority & Manning, PA (57) ABSTRACT

A core-shell nanoparticle is provided that includes a core comprising a first isotope of an element; an isolation layer surrounding the core; and a shell layer surrounding the isolation layer, wherein the shell layer comprises a second isotope of the element, with the first isotope being different than the second isotope. Methods are also provided for forming such core-shell nanoparticles.

12 Claims, 14 Drawing Sheets

(51) Int. Cl.
  *B01J 23/06* (2006.01)
  *B01J 23/50* (2006.01)
  *B82Y 15/00* (2011.01)
  *B01J 37/16* (2006.01)
  *B01J 23/66* (2006.01)
  *B01J 33/00* (2006.01)
  *B82Y 30/00* (2011.01)

(56) References Cited

OTHER PUBLICATIONS

Radloff & Halas, Plasmonic properties of concentric nanoshells, Nano Lett., vol. 4, No. 7, 2004, 1323-1327.*

Chugaev & Chernyshev, High-Noble measurement of 107Ag/109Ag in native silver and gold by multicollector inductively coupled plasma mass spectrometry, Geochemistry International, 2012, vol. 50, No. 11, 899-910.*

Prodan et al, A hybridization model for the plasmon resonse of complect nanostructures, Science, vol. 302, Oct. 2003, 419-422.*

Pena-Rodriguez & Pal, Enhanced plasmonic behavior of bimetallic (Ag-Au) multilayered spheres, Nanoscale Research Lett. 2011, 6:279.*

Tejamaya et al ("Stability of citrate, PVP, and PEG coated silver nanoparticles in ecotoxicology media", Environ. Sci. Technol. 2012, 46, 7011-7017).*

Romer et al., *Aggregation and dispersion of silver nanoparticles in exposure media for aquatic toxicity tests*, Journal of Chromatography A, 1218, 2011, pp. 4226-4233.

\* cited by examiner

| Particle type | Citrate | | | | PVP | |
|---|---|---|---|---|---|---|
| | Diameter nm (SD) | Roundness (SD) | | Diameter nm (SD) | | Roundness (SD) |
| Ag-109 | 3.68(0.58) | 0.73(0.05) | | 2.85(1.12) | | 0.70(0.05) |
| Ag(109)@Au | 7.14(0.87) | 0.81(0.03) | | 6.68(1.11) | | 0.79(0.04) |
| Ag(109)@Au@Ag(107) | 12.27(1.83) | 0.81(0.04) | | 10.24(2.01) | | 0.82(0.04) |

Fig. 7

| Particle type | Isotopic concentration (ppb) | | | | Isotopic ratio | |
|---|---|---|---|---|---|---|
| | Au | Ag(107) | Ag(109) | | Au/Ag(109) | Ag(107)/Ag(109) |
| Ag | 86.4 | 48551.6 | 48376.0 | | 0.002 | 1.004 |
| AgAu | 15561.0 | 3102.9 | 3169.9 | | 4.909 | 0.979 |
| AgAuAg | 6489.0 | 8297.8 | 8456.5 | | 0.767 | 0.981 |
| Ag109 | 167.9 | 88.4 | 9824.9 | | 0.017 | 0.009 |
| Ag109@Au | 11379.8 | 33.4 | 5122.9 | | 2.2 | 0.007 |
| Ag109@Au@Ag107 | 11253.4 | 8776.7 | 4659.0 | | 2.4 | 1.9 |

*Fig. 8*

CORE-SHELL NANOPARTICLES COMPRISING SAME ELEMENT OF DIFFERENT ISOTOPES

PRIORITY INFORMATION

The present application claims priority to U.S. Provisional Patent Application Ser. No. 61/983,807 titled "Novel Probes to Quantify the Relative Importance of Ion and Particle Uptake When Assessing Nanoparticle Bioavailability" of Lead, et al. filed on Apr. 24, 2014, the disclosure of which is incorporated by reference herein.

BACKGROUND

Nanoscience is the science of materials between approximately 1 and 100 nm in size; more importantly, at such sizes novel and size dependent behaviors reveal themselves. For instance, much work has been performed with nano-gold, where, at larger size scales, it is chemically inert. However, as size goes below about 10 nm, gold nanoparticles (NPs) become powerful catalysts and can be used, for example, in composites for environmental remediation. In addition, the optical properties of NPs change radically within the nano-range, because of interactions between incident light and surface electrons on the NP. Such behavior reveals itself in color changes as a function of size and is providing technology such as optically-based sensors.

Due to these novel properties, nanotechnology underpins a large and exponentially growing area of industry with global research and development investment of thousands of millions of dollars per year and global markets estimated in the trillions of dollars in the next few years. Current estimates suggest that there are many hundreds of NM-containing products on the market and this number is increasing linearly year on year. Currently consumer products are mainly at the low technology end of the sector e.g. carbon nanotubes used as structural materials, C60 fullerenes, titania and zinc oxide NPs used in cosmetics and sunscreens, Ag used as a bacteriocide in fabrics and elsewhere.

Given the large and increasing usage, environmental exposure is already occurring and likely to increase and models have been developed which have estimated exposure for a range of nanoparticles including nano-silver, nano-titania and carbon nanotubes, although data for model validation and parameterization is largely missing. In addition, bioaccumulation, toxicity or potential toxicity of a number of these materials have been established, but the mechanism of action or the important chemical species contributing to bioaccumulation and toxicity has not been established. In particular for metals and metal oxides the relative importance of the particle and ion phases in biouptake is variable for different nanoparticles but not quantitatively understood. Given the hazard and exposure, there is likely to be a risk to the environment and to human health, although this is very poorly characterized as yet including in terms of the bioaccumulated species. The long term sustainability of this highly beneficial industry requires greater understanding of the risks, minimization of these risks and that these risks are seen to be mitigated. In short, the impacts of NP dissolution on bioaccumulation and toxicity (along with fate and behavior) remain highly uncertain.

SUMMARY

Objects and advantages of the invention will be set forth in part in the following description, or may be obvious from the description, or may be learned through practice of the invention.

A core-shell nanoparticle is generally provided that includes, in one embodiment, a core comprising a first isotope of an element; an isolation layer surrounding the core; and a shell layer surrounding the isolation layer, wherein the shell layer comprises a second isotope of the element, with the first isotope being different than the second isotope.

Methods are also generally provided for forming such core-shell nanoparticles.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

In the present disclosure, when a layer is being described as "on" or "over" another layer or substrate, it is to be understood that the layers can either be directly contacting each other or have another layer or feature between the layers, unless expressly stated to the contrary. Thus, these terms are simply describing the relative position of the layers to each other.

As used herein, the prefix "nano" refers to the nanometer scale (e.g., from about 1 nm to about 100 nm). For example, particles having an average diameter on the nanometer scale (e.g., from about 1 nm to about 100 nm) are referred to as "nanoparticles."

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

It is to be understood that the use of "comprising" in conjunction with the embodiments described herein specifically discloses and includes the embodiments that "consist essentially of" the named components (i.e., contain the named components and no other components that significantly adversely affect the basic and novel features disclosed) and the embodiments that "consist of" the named components (i.e. contain only the named components except for contaminants which are naturally and inevitably present in each of the named components).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Novel isotopically-enriched core-shell NPs are generally disclosed. In one embodiment, the isotopically-enriched core-shell NPs can be used to quantify the respective roles of the particle and the ion from particle dissolution in bioaccumulation, depuration, environmental fate and other biological and environmental processes. The study of NPs and their bioavailability (and more generally their toxicity and environmental fate and behavior) is key to maintaining and improving ecological and human health and feeding back into the design of 'safe' NP, so this ability to understand mechanisms of behavior is important in both areas. Given the research expenditure and likely market, the materials are key emerging pollutants with potentially novel effects.

Figure 1:
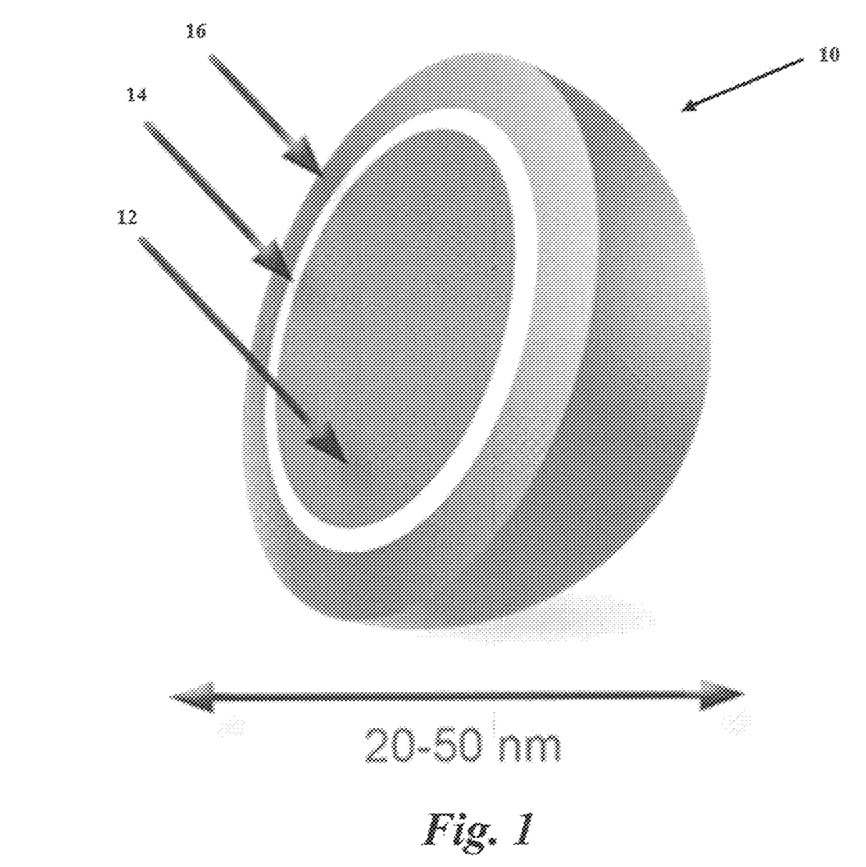
FIG. 1 shows a diagram of an exemplary core-shell nanoparticle according to one embodiment.

Referring to FIG. 1, an exemplary core-shell nanoparticle 10 is shown according to one embodiment of the present application. The core-shell nanoparticle 10 includes a core 12, an isolation layer 14 surrounding the core 12, and a shell layer 16 surrounding the isolation layer 14. According to this construction, the first isotope of the core 12 is separated from the second isotope in the shell layer 16 by the isolation layer 14.

Generally, the core 12 includes a first isotope of an element, and the shell layer includes a second isotope of the element that is different than the first element. For example, in one embodiment, the core include $^{67}Zn$ (i.e., the isotope of zinc having an atomic mass of 67) and the shell layer includes $^{68}Zn$ (i.e., the isotope of zinc having an atomic mass of 68), in another embodiment, the core includes $^{107}Ag$ (i.e., the isotope of silver having an atomic mass of 107), and the shell layer includes $^{109}Ag$ (i.e., the isotope of silver having an atomic mass of 109). Of course, any suitable material having at least two stable isotopes can be utilized in the core-shell nanoparticle 10. Additionally, the isotope may be included in the core 12 and/or shell layer 16 in its elemental state and/or in a compound. For example, cerium oxide (e.g., $CeO_2$ and/or $Ce_2O_3$) may be included in the core 12 as cerium 140 and in the shell layer 16 as cerium 142, or vice versa. Other cerium isotopes can also be utilized (e.g., cerium 138 and/or cerium 136).

Figure 2:
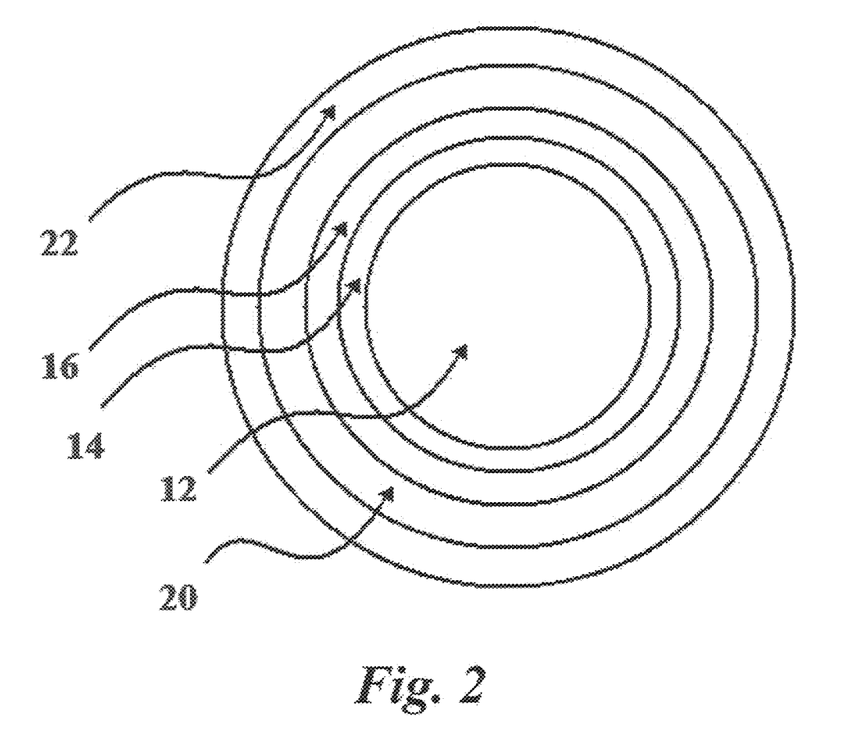
FIG. 2 shows a cross-section of an exemplary multi-layer coating of an exemplary core-shell nanoparticle according to one embodiment.

With elements that have more than two isotopes, it is also possible to form a multilayered nanoparticle having at least 3 isotopes present, with each isotope separated by an intermediate layer from each other. Referring to the multilayered nanoparticle of FIG. 2, for example, a nanoparticle is shown having second isolation layer 20 on the shell layer 16, and a second shell layer 22 on the second isolation layer 20. The second shell layer includes an isotope of the element that is different than the first isotope in the core 12, the second isotope in the shell layer 16, or both. Additional layers can be formed on the nanoparticle as desired in a similar manner.

Figure 3:
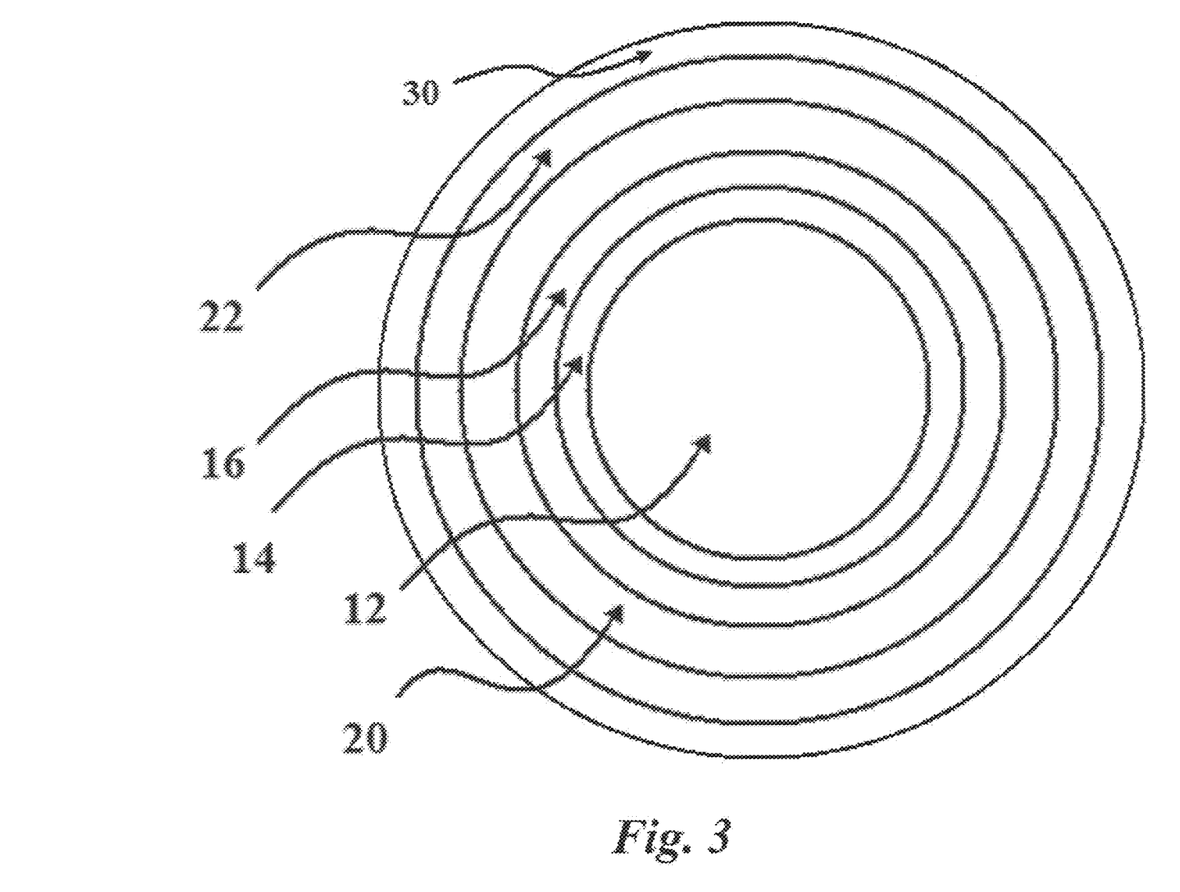
FIG. 3 shows a cross-section of an exemplary multi-layer nanoparticle having a polymeric shell thereon according to one embodiment.

FIG. 3 shows another embodiment that includes a polymeric outer layer 30 on the nanoparticle's outer surface. As shown, the polymeric outer layer 30 can be positioned on the optional second shell layer 22 (if present), or may be positioned directly on the shell layer 16. In particular embodiments, the polymeric outer layer 30 can form an outer surface of the nanoparticle. Alternatively, additional layers may be positioned on the nanoparticle, depending on the desired use.

The polymeric outer layer 30 may be configured to stabilize the nanoparticle in a particular media. For example, the polymeric outer layer 30 can form a polymeric nanoparticle shell from a polymeric material that comprises at least one polymer. In one particular embodiment, the polymeric sheath can have a thickness of about 1 nm to about 50 nm on the core. The polymeric sheath may be chemically bonded to the core, and/or may be mechanically bonded around the inner layers of the nanoparticle depending on the interaction between the particular polymeric material utilized and the adjacent layers present.

In one embodiment, the polymeric nanoparticle shell can include a polyvinylpyrrolidone-based polymer (e.g., a PVP-based polymer), either alone or in a polymeric matrix with another polymer, such as disclosed in U.S. Patent Application Ser. No. 61/942,154 titled "Separation of Oil-Water Mixtures Using Nanotechnology" of Lead, et al. filed on Feb. 20, 2014, which is incorporated herein by reference.

Although PVP is found to provide nanoparticles with most environmentally stable attributes, other polymers, macromolecules, and organic anions may be used in the polymeric shell to stabilize the nanoparticles. For example, citrate can be used in the synthesis of the polymeric material and may be retained to electrostatically stabilize the nanoparticles, or is easily displaced by other polymeric or macromolecular ligand groups. Polyethylene glycol (PEG) and variants can also be used to colloidally stabilize nanoparticles and can displace citrate after synthesis. In addition, the group of naturally occurring organic macro-ions known as humic substances (which can be further separated into humic acids and fulvic acids) can be used both in synthesis of metal nanoparticles and in the replacement of citrate and stabilization of nanoparticles via electrosteric mechanisms.

EXAMPLES

Based on the summary of the current state of the art in the Background section above, the following question is relevant and timely: Is NP bioaccumulation and bioavailability (and related biological and environmental process) mediated by the particle or by dissolution? In other words, are the nanoparticles themselves taken up by and removed from tissues or cells or do NPs act to deliver high concentrations of bioavailable 'dissolved' metal into or onto the organism? In addition, wider questions related to particle and ion fate and behavior in environmental, biological and human systems may be answered definitively using this tracer.

It is hypothesized, without wishing to be bound by any particular theory, that bioaccumulation, which is here used as a proxy for bioavailability, is controlled by direct uptake of the NP. In order to study this hypothesis, novel isotopically labeled, core-shell tracers are disclosed herein for the limiting cases of soluble and insoluble NPs and an intermediate case of partially soluble NPs. Thus, particles with a range of properties (size, core composition, surface coating) can be examined to quantify the effect of particle property. In addition, the effect can be investigated in different exposure scenarios including waterborne and dietborne exposure. Elimination (form the organism) studies can also be included. The use of the combination of isotopically labeled, core-shell NPs allows one to distinguish dissolved and particle behavior and has two other significant advantages: 1) engineered NPs will be more easily distinguishable from natural background levels, and 2) engineered NPs in organisms after exposure can be traced at realistic concentrations, rather than the higher exposure levels currently used to circumvent the lack of suitable tracing techniques.

Thus, the presently disclosed nanoparticles have the potential for wider use as tracers to investigate fate and transport in human, biological and environmental systems. For example, the nanoparticles discussed herein can be useful as a tracer for fate/behavior in many systems (as above), such as to study transport, persistence, transformations as well as bioaccumulation. Thus, these materials can be transformative, fundamental, with many applied aspects, and cross-disciplinary. The development of novel methodological tools (core-shell, isotopically labeled NPs) and provision of an answer to the fundamental question related to ion or particle bioavailability is of key importance in nanotoxicology and environmental nanoscience. In addition to further quantifying the nature of bioavailability, it is possible that the core-shell, labeled NPs have uses in more routine bioaccumulation studies, in helping to better understand toxicity and having applications in environmental fate studies.

Synthesis

A number of synthesis methods use organic solvents such as ethanol or chloroform and other chemicals, which can provide equally monodisperse NPs, but potentially introduce adverse biological effects in addition to the NP if used in exposure studies. Even with extensive clean up procedures, there is still be uncertainty. As such, in preferred embodiments, aqueous synthesis using biocompatible materials only and using only aqueous suspensions is generally provided. In addition, synthesis can be performed under sterile condition to as far as possible minimize any potential bacterial alterations and contamination with endotoxin.

The production of NPs, including zinc oxide, silver, and cerium oxide can be achieved (see, e.g., FIGS. 4a-4d). Detailed methodologies have been used and developed by the inventors and their research group for NP synthesis using simple synthetic methods, which are tightly controlled and optimized to produce batches of NPs with highly constrained properties (example results provided). As an example, a useful methodology is to take the standard and very simple method of silver nitrate reduction using suitable reductant and citrate as a capping agent. The highly labile citrate is easily replaced by polymeric or macromolecular coatings such as the previously mentioned PVP, or PEG, humic substances or others. This results in particles which are generally identical in all aspects except the capping agent, making a direct comparison of coating, with minimal confounding factors, possible. In order to produce differently shaped particles, a number of methods are available in the literature. For example, methods including the production of silver prisms in the presence of citrate and PVP, followed by controlled oxidation using nitrate or hydrogen peroxide and the production of ceria rods by controlling pH, precursors, reaction conditions and other parameters.

The differently labeled NMs can be doped separately into food and water to help understand the importance of the two different exposure routes. For instance, highly enriched Zn-67 can be put into feed, while Zn-68 can be doped into exposure waters. Separate feed and waterborne exposures as controls and subsequently combined exposures will be used. Core-shell materials have been described in the literature (see FIGS. 4b and 4c for concept using Ag and Zn isotopes) and the isotopically enriched core-shell NPs can be used directly to assess the relative importance of particle and ion uptake. In one embodiment, core-shell particles of three layers can be synthesized, with the central layer made of insoluble material (such as gold, silica or potentially ceria). Uptake of the enriched core suggests particle delivery, while uptake of the outer core reflects both dissolution and ion uptake processes. Tracing dissolution and solubility processes as well as uptake processes (biodynamic modeling, see below) using measurements of isotopic ratios will permit full quantification of particle uptake and dissolved ion uptake.

Methods

An exemplary method used to produce three layer nanoparticle (Ag core, Au inner layer, Ag shell, abbreviated: Ag—Au—Ag) is given in detail.

The method used to produce Ag-seeds (cores) of about 10 nm was as follows:

1. Solutions of 100 ml of 0.25 mM $AgNO_3$, 100 ml 0.31 mM Sodium citrate, 6 ml 2.5 mM $NaBH_4$ (1.5 ml 10 mM $NaBH_4$ and 4.5 mM $H_2O$) were refrigerated for 30 minutes until all solutions are were 4° C.
2. The sodium citrate and silver nitrate were combined together while stirring,
3. The $NaBH_4$ solution was added, and the mixture stirred for 10 minutes while cold and heated.
4. The mixture was then refluxed for 1 hour.

5. The mixture was then cooled to room temperature and left for 12 hours.
6. The resulting suspension was ultrafiltered 3 to 5 times using a diafiltration approach.
7. The resulting solution was then filtered through a 100 nm filter to remove any large particles.

Ag—Au NP Production
1. 200 ml Ag seed NPs were heated to 60° C. and stirred gently.
2. 15 ml of gold chloride (0.2 mM gold chloride solution) was added to the suspension slowly in a drop wise fashion at a rate of 0.2 ml/minute.
3. The mixture was stirred for 30 minutes after the gold chloride solution was added.
4. The resulting mixture was cooled to room temperature, and left for 12 hours.
5. The particles were washed in a similar manner to the seed particles.

Ag—Au—Ag NP Production
1. A solution of the 200 ml Ag—Au NPs was heated to 100° C. with vigorous stirring.
2. 25 ml each of 20 mM $AgNO_3$ and 0.25 mM sodium citrate were added simultaneously to the suspension slowly in a drop wise fashion at a rate of 1 ml every 10 minutes.
3. The resulting mixture was stirred for 15 minutes after the addition of $AgNO_3$ and sodium citrate.
4. The resulting mixture was cooled to room temperature, and left for 12 hours.
5. The particles were washed as in the Ag seed production process.

Results

FIGS. 4-8 show data on Ag@Au core-shell particles produced using the facile method suitable for biological studies; hydrothermal synthesis uses no solvents, high purity materials, tightly controlled reaction conditions leading to tightly constrained material properties with few possible confounding factors. FIG. 4a shows shifts in surface plasmon peaks at 400 nm (Ag NPs) and 520 nm (gold), with the Ag seed particle having a peak at 400 nm and AgAu-7 having a peak at 520 mm. Corresponding hydrodynamic sizes (dynamic light scattering data) are given in FIG. 4b, showing the growth from 15 to 30 nm. FIGS. 5a and 5c show STEM images of $^{109}$Ag@Au@$^{107}$Ag-Citrate and $^{109}$Ag@Au@$^{107}$Ag-PVP, respectively.

Figure 4A:
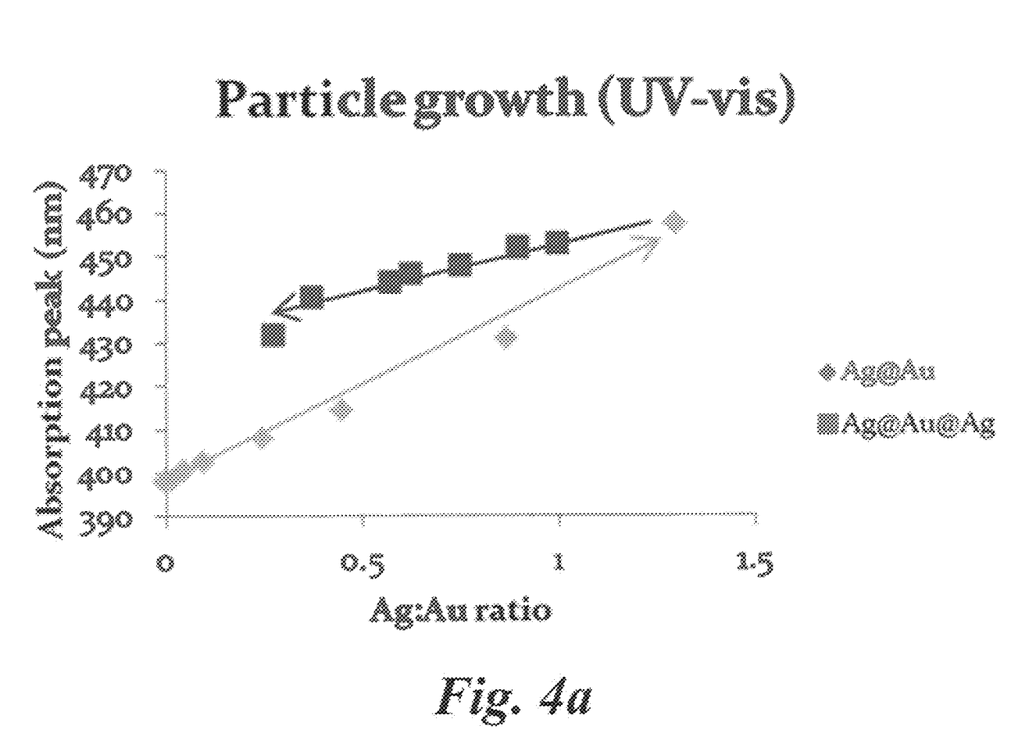
FIG. 4a shows the ratio of Ag:Au concentration during the Au barrier layer growth (diamonds) and addition of Ag outer layer (squares), measured by UV-vis spectra.
Figure 4B:
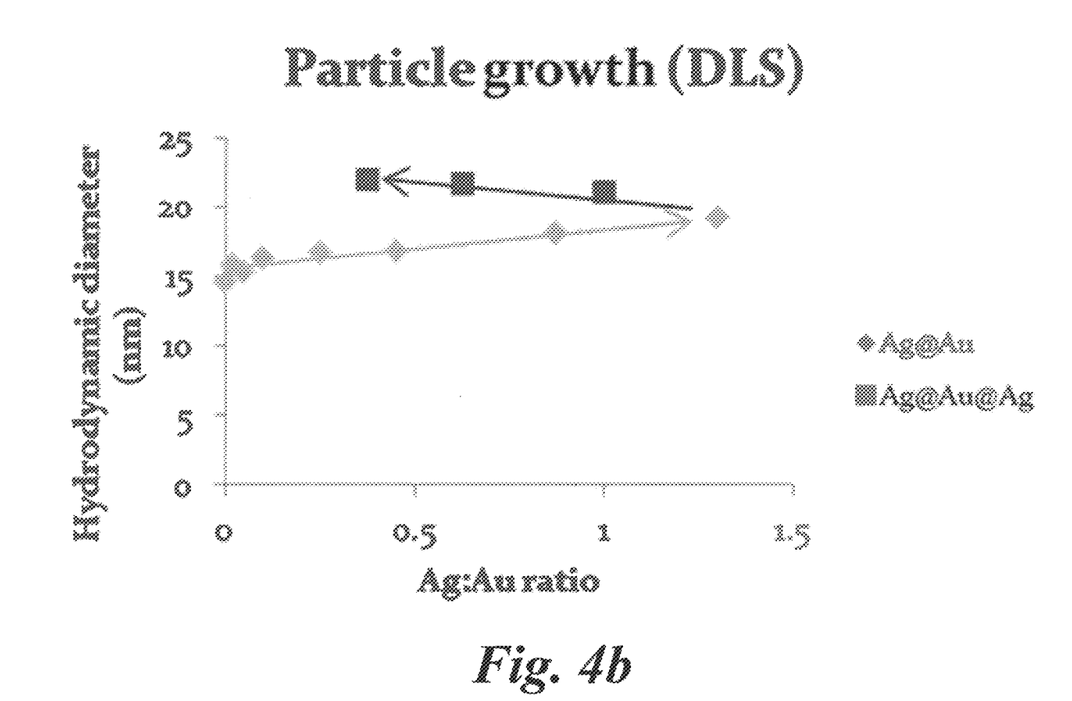
FIG. 4b shows the ratio of Ag:Au concentration during the Au barrier layer growth (diamonds) and addition of Ag outer layer (squares), measured by DLS spectra.
Figure 5A:
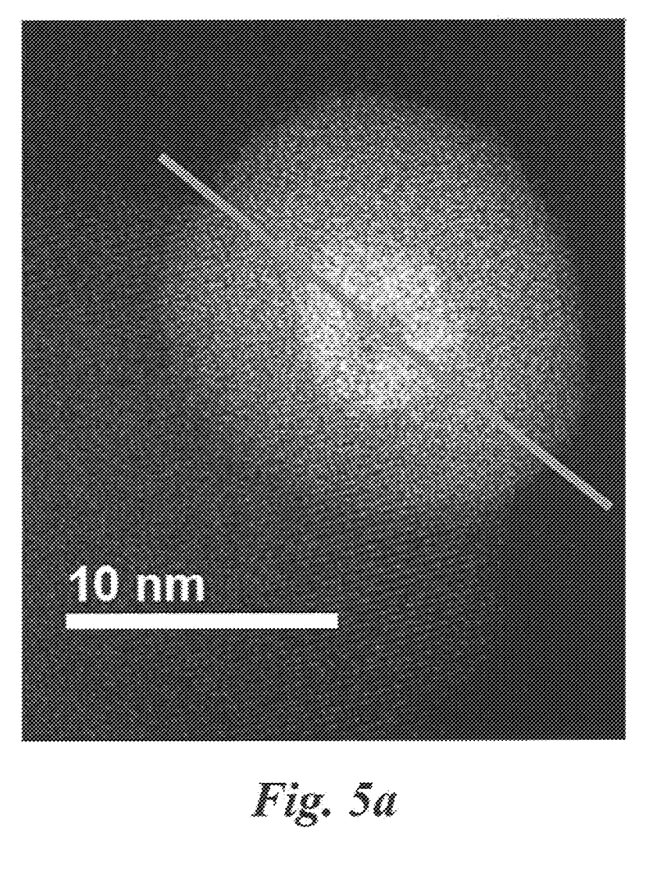
FIG. 5a shows a typical STEM image of $^{109}$Ag@Au@$^{107}$Ag-Citrate.
Figure 5B:
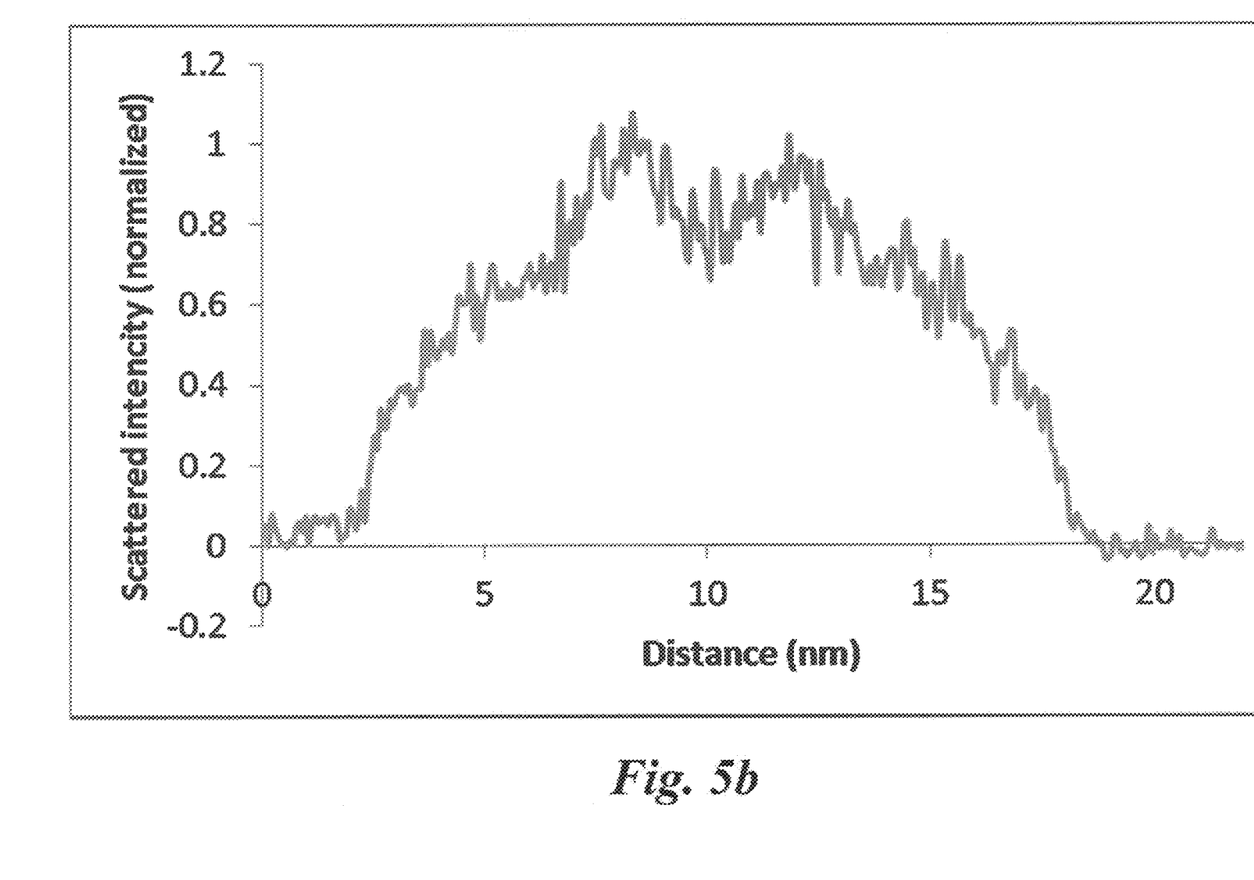
FIG. 5b shows the size distribution of the $^{109}$Ag@Au@$^{107}$Ag-Citrate particles according to the Examples.
Figure 5C:
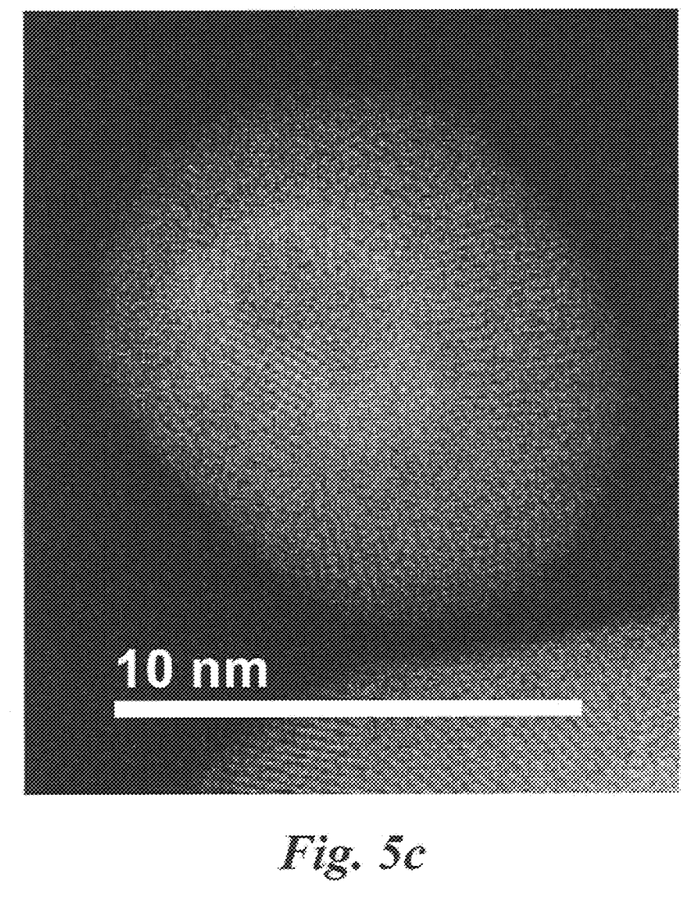
FIG. 5c shows a typical STEM image of $^{109}$Ag@Au@$^{107}$Ag-PVP.
Figure 5D:
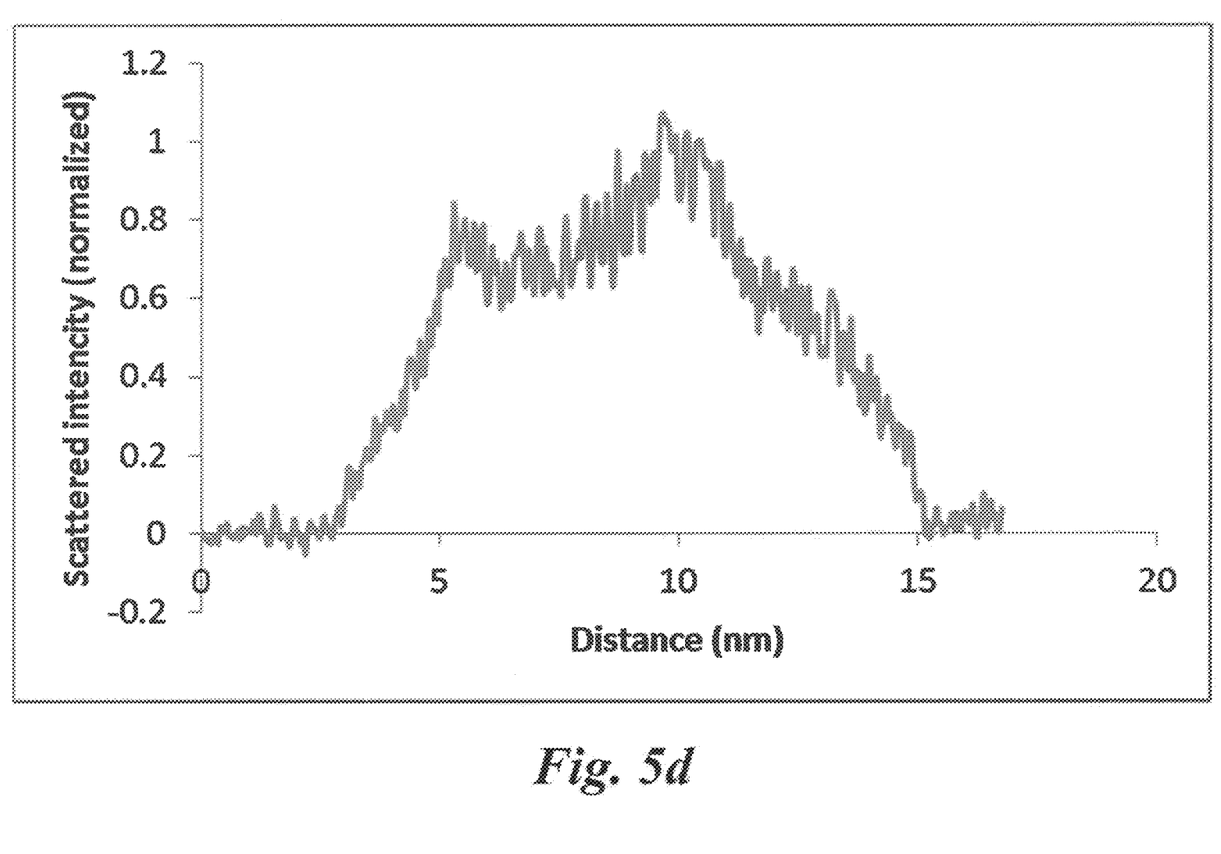
FIG. 5d shows the size distribution of the $^{109}$Ag@Au@$^{107}$Ag-PVP particles according to the Examples.
Figure 6A:
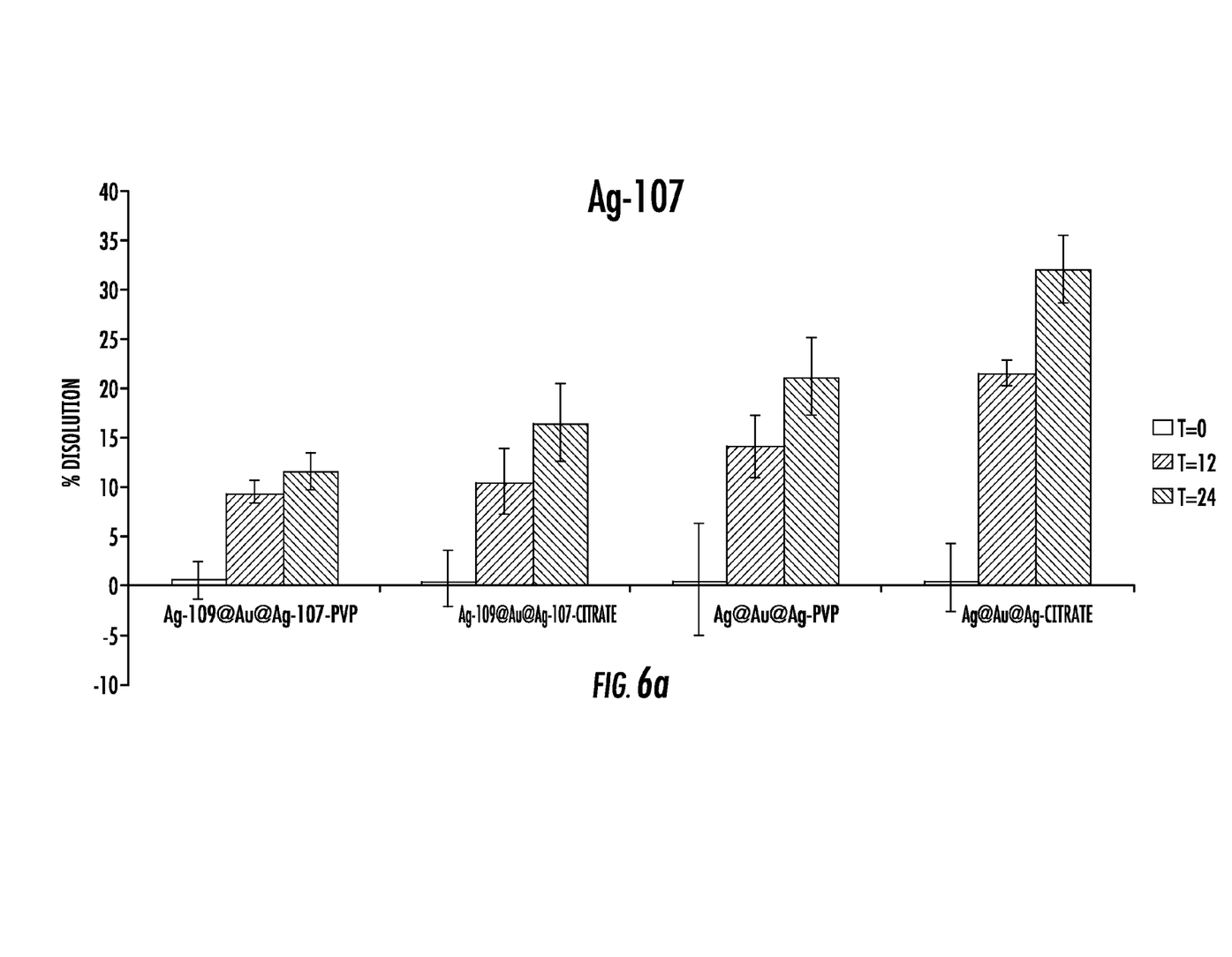
FIG. 6a shows a comparison of the percentage dissolution of the different isotopes at 0 (left bar) 12 (middle bar) and 24 (right bar) hours for $^{107}$Ag.
Figure 6B:
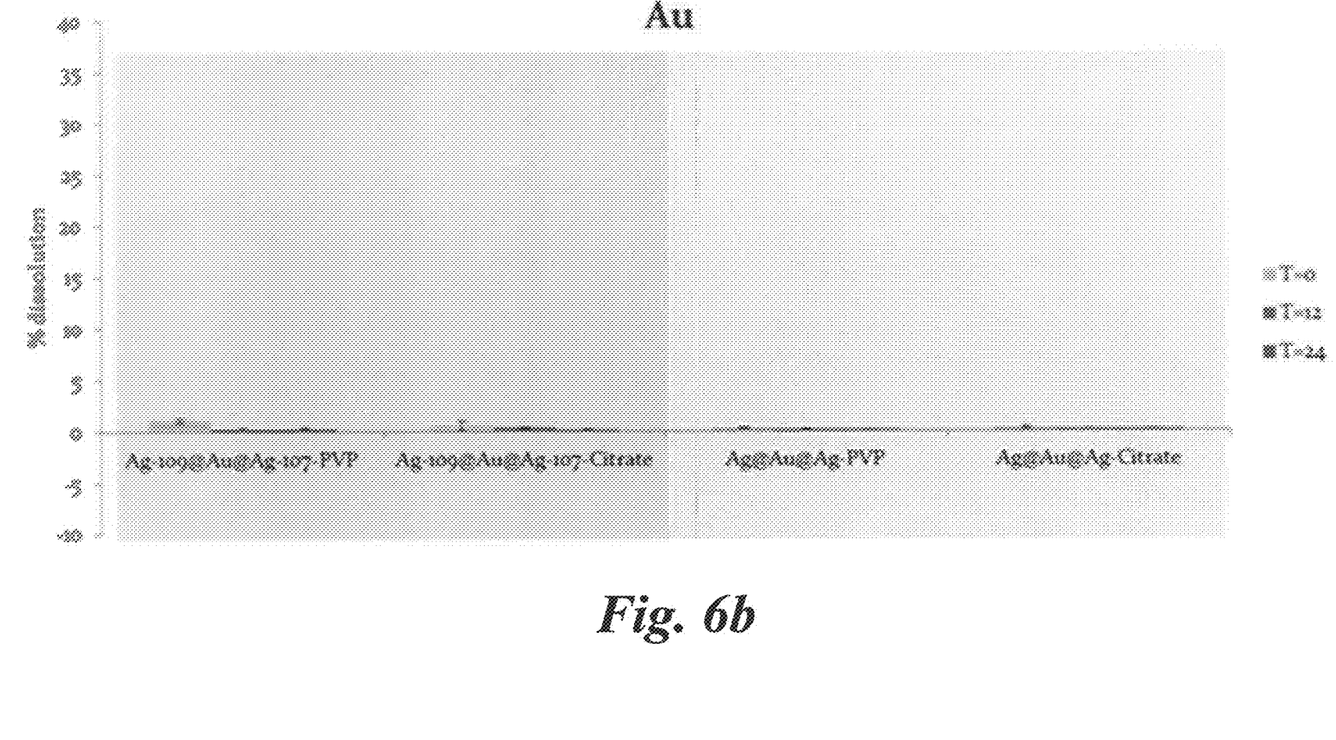
FIG. 6b shows a comparison of the percentage dissolution of the different isotopes at 0 (left bar) 12 (middle bar) and 24 (right bar) hours for Au.
Figure 6C:
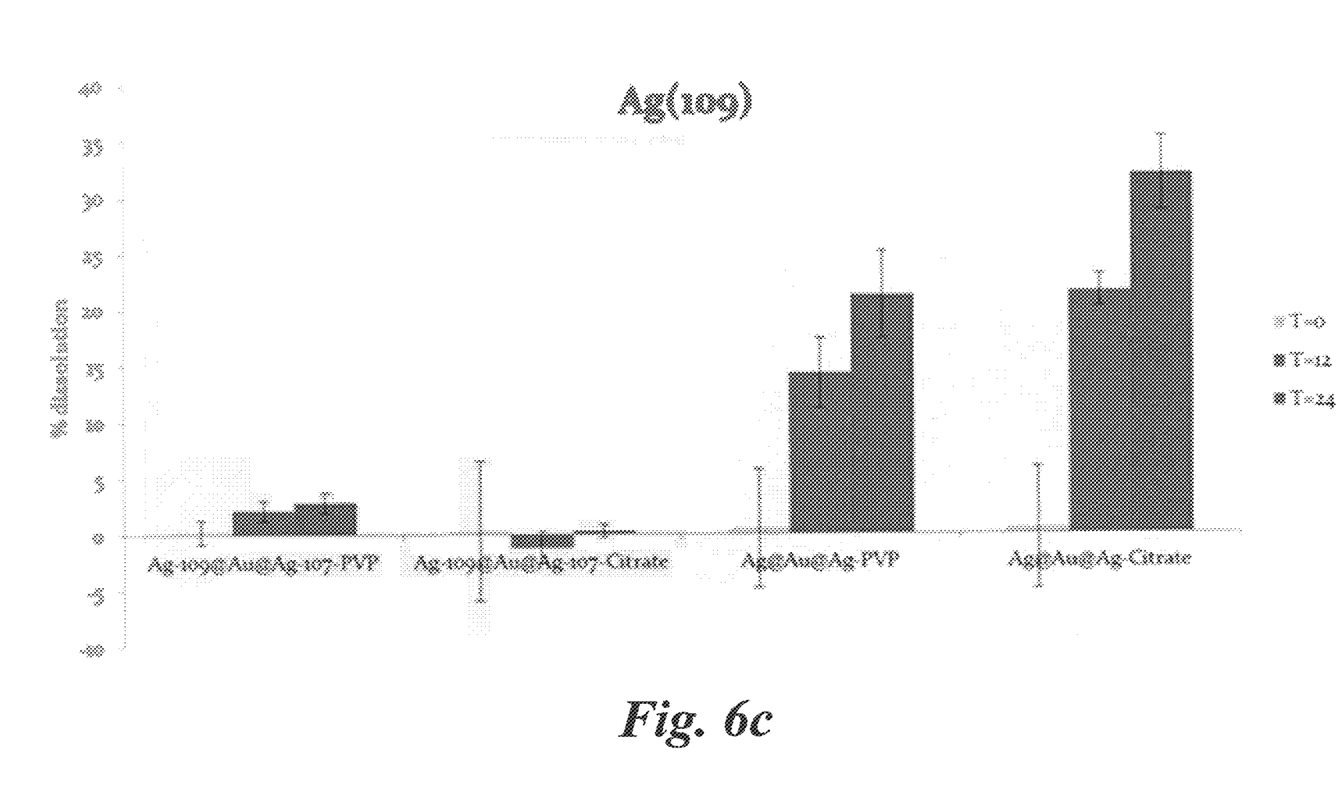
FIG. 6c shows a comparison of the percentage dissolution of the different isotopes at 0 (left bar) 12 (middle bar) and 24 (right bar) hours for $^{109}$Ag.
Figure 7:
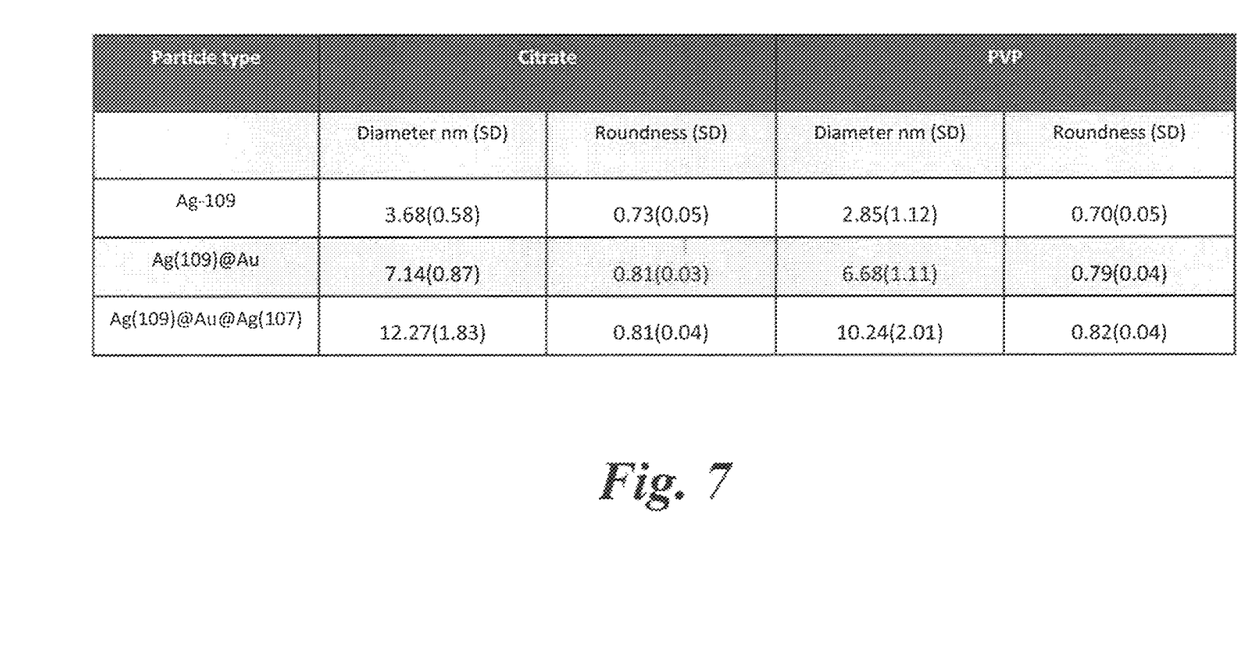
FIG. 7 shows a table of the tabulated results of the diameters of the $^{109}$Ag, $^{109}$Ag@Au and @Ag@Au@$^{107}$Ag and roundness as measured from the STEM images. Citrate and PVP refer to the external coating to ensure colloidal stabilization. SD is measured standard deviation.
Figure 8:
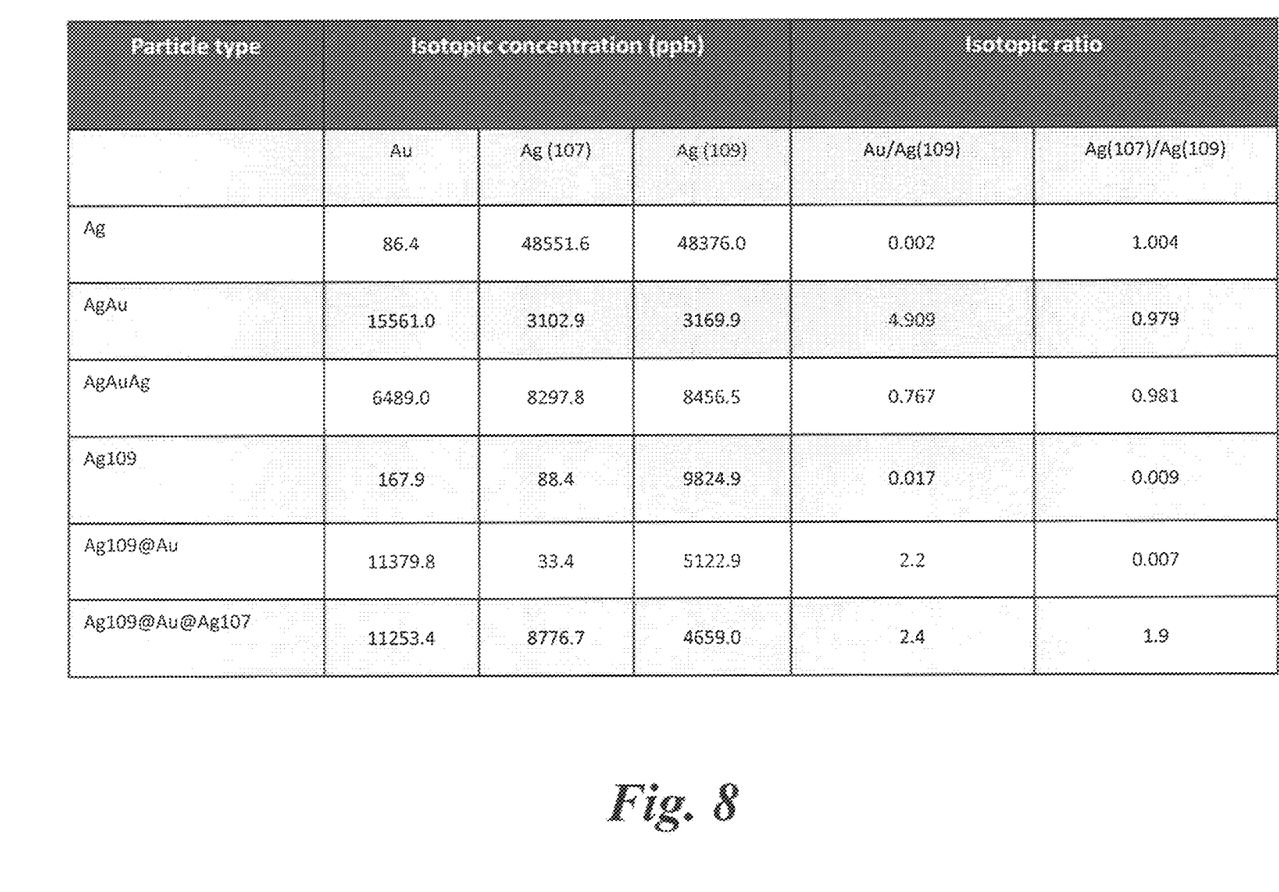
FIG. 8 shows a table of the concentrations of $^{107}$Ag, $^{109}$Ag and Au as measured from ICP-MS for the separate layers of the non-labeled and labeled NPs.

FIG. 4a shows the UV-Vis absorbance data of the Ag—Au particle, and the Ag—Au—Ag particle from separate batches. FIG. 4b shows the dynamic light scattering (DLS) data.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A core-shell nanoparticle, comprising:
a core comprising a first isotope of silver;
an isolation layer surrounding the core; and
a shell layer surrounding the isolation layer, wherein the shell layer comprises a second isotope of silver, with the first isotope being different than the second isotope.

2. The nanoparticle as in claim 1, wherein the isolation layer comprises a material that is substantially free from the element.

3. The nanoparticle as in claim 1, wherein the first isotope is $^{107}$Ag, and wherein the second isotope is $^{109}$Ag.

4. The nanoparticle as in claim 1, wherein the first isotope is $^{109}$Ag, and wherein the second isotope is $^{107}$Ag.

5. The nanoparticle as in claim 1, wherein the isolation layer comprises gold.

6. The nanoparticle as in claim 1, wherein the isolation layer comprises silicon.

7. The nanoparticle as in claim 6, wherein the isolation layer comprises silicon dioxide.

8. The nanoparticle as in claim 1, further comprising:
a second isolation layer on the shell layer; and
a second shell layer on the second isolation layer, wherein the second shell layer comprises a third isotope of silver, with the third isotope being different than the first isotope, the second isotope, or both.

9. The nanoparticle as in claim 8, further comprising:
a third isolation layer on the second shell layer; and
a third shell layer on the third isolation layer, wherein the third shell layer comprises a fourth isotope of silver, with the fourth isotope being different than the first isotope, the second isotope, and/or the third isotope.

10. The nanoparticle as in claim 1, further comprising:
a polymeric outer layer positioned to define an outer surface on the nanoparticle.

11. The nanoparticle as in claim 10, wherein the polymeric outer layer comprises a polyvinylpyrrolidone-based polymer.

12. The nanoparticle as in claim 10, wherein the polymeric outer layer comprises citrate.

* * * * *